United States Patent
Song et al.

(10) Patent No.: US 10,201,668 B2
(45) Date of Patent: Feb. 12, 2019

(54) AUTOMATIC NEEDLE INSERTION APPARATUS

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yubing Song, Beijing (CN); Jing Xue, Beijing (CN); Yanyan Yin, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 363 days.

(21) Appl. No.: 15/167,501

(22) Filed: May 27, 2016

(65) Prior Publication Data
US 2017/0028142 A1 Feb. 2, 2017

(30) Foreign Application Priority Data

Jul. 31, 2015 (CN) .......................... 2015 1 0463281

(51) Int. Cl.
| | |
|---|---|
| *A61M 5/42* | (2006.01) |
| *A61B 8/06* | (2006.01) |
| *A61M 5/20* | (2006.01) |
| *A61B 8/08* | (2006.01) |
| *A61M 5/158* | (2006.01) |

(52) U.S. Cl.
CPC ............ *A61M 5/427* (2013.01); *A61B 8/0841* (2013.01); *A61M 5/20* (2013.01); *A61B 8/488* (2013.01); *A61M 2005/1585* (2013.01); *A61M 2205/10* (2013.01); *A61M 2209/08* (2013.01)

(58) Field of Classification Search
CPC .......... A61M 5/427; A61M 2005/1583; A61M 2005/1586; A61M 2205/10;
(Continued)

(56) References Cited

U.S. PATENT DOCUMENTS

| | | | | |
|---|---|---|---|---|
| 4,351,335 A | * | 9/1982 | Whitney ........... | A61M 5/14546 128/DIG. 1 |
| 9,808,579 B2 | * | 11/2017 | Hyde ...................... | A61M 5/30 |

(Continued)

FOREIGN PATENT DOCUMENTS

| | | |
|---|---|---|
| CN | 1612711 A | 5/2005 |
| CN | 1671428 A | 9/2005 |

(Continued)

OTHER PUBLICATIONS

English translation of JP 2014-239831.*
(Continued)

*Primary Examiner* — Nathan R Price
*Assistant Examiner* — Courtney B Frederickson
(74) *Attorney, Agent, or Firm* — Harness, Dickey & Pierce, P.L.C.

(57) ABSTRACT

The present disclosure provides an automatic needle insertion apparatus, including a frame, a bearing device on the frame and configured to bear thereon a body part into which a needle is to be inserted, an acquisition device on the frame and configured to acquire vascular information of the body part, a needle insertion device on the frame and configured to execute a needle insertion operation and a needle withdrawal operation on the body part, and a first control device connected to the needle insertion device and the acquisition device and configured to control an operating state of the needle insertion device in accordance with the vascular information acquired by the acquisition device.

9 Claims, 3 Drawing Sheets

(58) Field of Classification Search
CPC .. A61M 2209/08; A61B 8/0841; A61B 90/57; A61B 90/10; A61B 2019/101; A61B 90/11; A61B 90/14
See application file for complete search history.

(56) References Cited

U.S. PATENT DOCUMENTS

| | | | |
|---|---|---|---|
| 2003/0120283 A1 | 6/2003 | Stoianovici et al. | |
| 2006/0079768 A1 | 4/2006 | Small et al. | |
| 2006/0167415 A1 | 7/2006 | Nemoto | |
| 2008/0275396 A1 | 11/2008 | Neerken et al. | |
| 2009/0177188 A1 | 7/2009 | Steinkogler | |
| 2010/0010505 A1* | 1/2010 | Herlihy | A61B 90/11 606/130 |
| 2010/0168535 A1* | 7/2010 | Robinson | A61B 5/14532 600/309 |
| 2010/0274202 A1* | 10/2010 | Hyde | A61B 10/0283 604/272 |

FOREIGN PATENT DOCUMENTS

| | | | |
|---|---|---|---|
| CN | 101039711 A | 9/2007 | |
| CN | 101171046 A | 4/2008 | |
| CN | 101267854 A | 9/2008 | |
| CN | 101632596 A | 1/2010 | |
| CN | 102018497 A | 4/2011 | |
| CN | 102098367 A | 6/2011 | |
| CN | 102406972 A | 4/2012 | |
| CN | 204181629 U | 3/2015 | |
| JP | 2014239831 A | * 12/2014 | ............ A61M 5/142 |
| KR | 101452631 B1 | 10/2014 | |

OTHER PUBLICATIONS

First Office Action regarding Chinese Application No. 201510463281.9, dated Sep. 13, 2017. Translation provided by Dragon Intellectual Property Law Firm.

* cited by examiner

US 10,201,668 B2

AUTOMATIC NEEDLE INSERTION APPARATUS

CROSS-REFERENCE TO RELATED APPLICATION

The present application claims a priority of the Chinese patent application No. 201510463281.9 filed on Jul. 31, 2015, which is incorporated herein by reference in its entirety.

TECHNICAL FIELD

The present disclosure relates to the field of medical equipment, in particular to an automatic needle insertion apparatus.

BACKGROUND

Recently, more and more people become sub-healthy, and sometimes they need to have an injection, an intravenous drip or bloodletting, resulting in an increase in the workload of nurses and a drop in the work efficiency. In addition, in the case that the nurses are tired, errors may easily occur during the injection, infusion or bloodletting.

SUMMARY

An object of the present disclosure is to provide an automatic needle insertion apparatus, so as to insert a needle automatically, thereby to improve the work efficiency and reduce human errors.

In one aspect, the present disclosure provides in some embodiments an automatic needle insertion apparatus, including: a frame; a bearing device on the frame and configured to bear thereon a body part into which a needle is to be inserted; an acquisition device on the frame and configured to acquire vascular information of the body part; a needle insertion device on the frame and configured to execute a needle insertion operation and a needle withdrawal operation on the body part; and a first control device connected to the needle insertion device and the acquisition device and configured to control an operating state of the needle insertion device in accordance with the vascular information acquired by the acquisition device.

Alternatively, the acquisition device includes: an ultrasound image processing unit configured to send an ultrasound pulse to the body part, generate first image data in accordance with an ultrasound signal from the body part, and acquire the vascular information of the body part in accordance with the first image data; and/or an infrared scanning unit configured to generate second image data in accordance with an infrared ray radiated by the body part, and acquire the vascular information of the body part in accordance with the second image data.

Alternatively, the needle insertion device includes: a syringe; and a mechanical arm configured to grip the syringe and adjust a position of a needle of the syringe and control the syringe to execute the needle insertion operation and the needle withdrawal operation. The first control device includes: a storage circuit configured to store therein different predetermined needle insertion modes; and a first control circuit connected to the mechanical arm, and configured to control the mechanical arm to adjust the position of the needle of the syringe and execute the needle insertion operation and the needle withdrawal operation in accordance with the vascular information of the body part and a current predetermined needle insertion mode.

Alternatively, the needle insertion device further includes: a piston rod operation member connected to a piston rod of the syringe and configured to control a push-and-pull state of the piston rod of the syringe. The first control device further includes: a second control circuit connected to the piston rod operation member and configured to control an operating state of the piston rod operation member of the syringe in accordance with the current predetermined needle insertion mode, so as to control the push-and-pull state of the piston rod of the syringe.

Alternatively, the piston rod operation member includes: a driving motor; and a transmission rod connected between the driving motor and the piston rod. The second control circuit is configured to control an operating state of the driving motor in accordance with the predetermined needle insertion mode, so as to control the push-and-pull state of the piston rod.

Alternatively, the piston rod operation member further includes a stroke definition groove, into which one end of the piston rod connected to the transmission rod is arranged, and which is configured to define a movement stroke of the piston rod, so as to prevent the piston rod from being offset during a push-and-pull procedure.

Alternatively, the automatic needle insertion apparatus further includes: a plurality of liquid storage tanks configured to store liquids therein, the liquids being delivered into different syringes from different liquid storage tanks; and a control valve configured to control on and off states between each liquid storage tank and the corresponding syringe. The first control device further includes: a first mode switch circuit configured to send a control signal to the second control circuit in accordance with the current predetermined needle insertion mode, so as to control the mechanical arm to adjust the position of the needle of the syringe corresponding to the current predetermined needle insertion mode and execute the needle insertion operation and the needle withdrawal operation; and a second mode switch circuit configured to control an operating state of the control valve, so as to enable the liquid storage tank corresponding to the current predetermined needle insertion mode to be in communication with the syringe corresponding to the current predetermined needle insertion mode.

Alternatively, the automatic needle insertion apparatus further includes: an adhesive bandage application device configured to apply an adhesive bandage at a position of the body part into which the needle is inserted by the needle insertion device before the needle withdrawal operation is executed by the needle insertion device; and a second control device configured to, in accordance with the vascular information of the body part, adjust a position of the adhesive bandage application device and control the adhesive bandage application device to execute an adhesive bandage application operation.

Alternatively, the automatic needle insertion apparatus further includes an adjustment device connected to the bearing device and configured to adjust a position of the bearing device, so as to move the body part to a predetermined position.

Alternatively, the adjustment device includes: supporters connected to two sides of the bearing device respectively; sliding rails arranged on the frame and located at two sides of the bearing device, the supporters being movably arranged onto the sliding rails respectively; and stoppers arranged on the frame and configured to limit positions of the supporters on the sliding rails in the case that the bearing device moves to a predetermined position.

Alternatively, the automatic needle insertion apparatus further includes a blood storage tank configured to store therein blood drawn from the body part.

Alternatively, the automatic needle insertion apparatus further includes a sterilization device and a third control device configured to, in accordance with the vascular information of the body part, adjust a position of the sterilization device and control the sterilization device to execute a sterilization operation.

Alternatively, the bearing device is an inflatable air bag with a pressure sensor.

According to the automatic needle insertion apparatus in the embodiments of the present disclosure, it is able to automatically insert the needle in accordance with the information of a vessel position and a vessel depth, thereby to reduce the human errors and improve the working efficiency.

DETAILED DESCRIPTION OF THE EMBODIMENTS

The present disclosure will be described hereinafter in conjunction with the drawings and embodiments. The following embodiments are for illustrative purposes only, but shall not be used to limit the scope of the present disclosure.

An object of the present disclosure is to provide an automatic needle insertion apparatus, so as to insert a needle automatically, reduce the human errors and improve the working efficiency.

Figure 1:
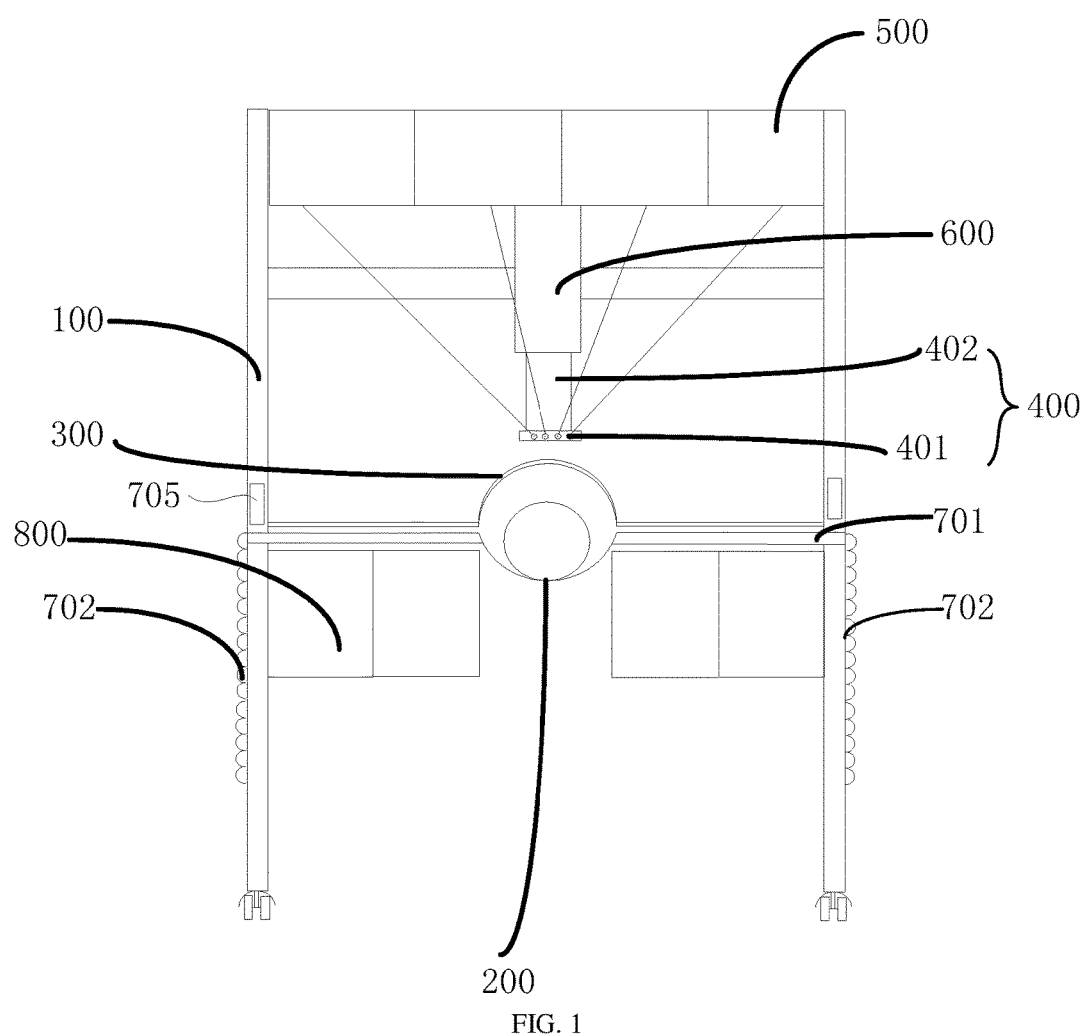
FIG. 1 is a front view of an automatic needle insertion apparatus according to one embodiment of the present disclosure.
Figure 2:
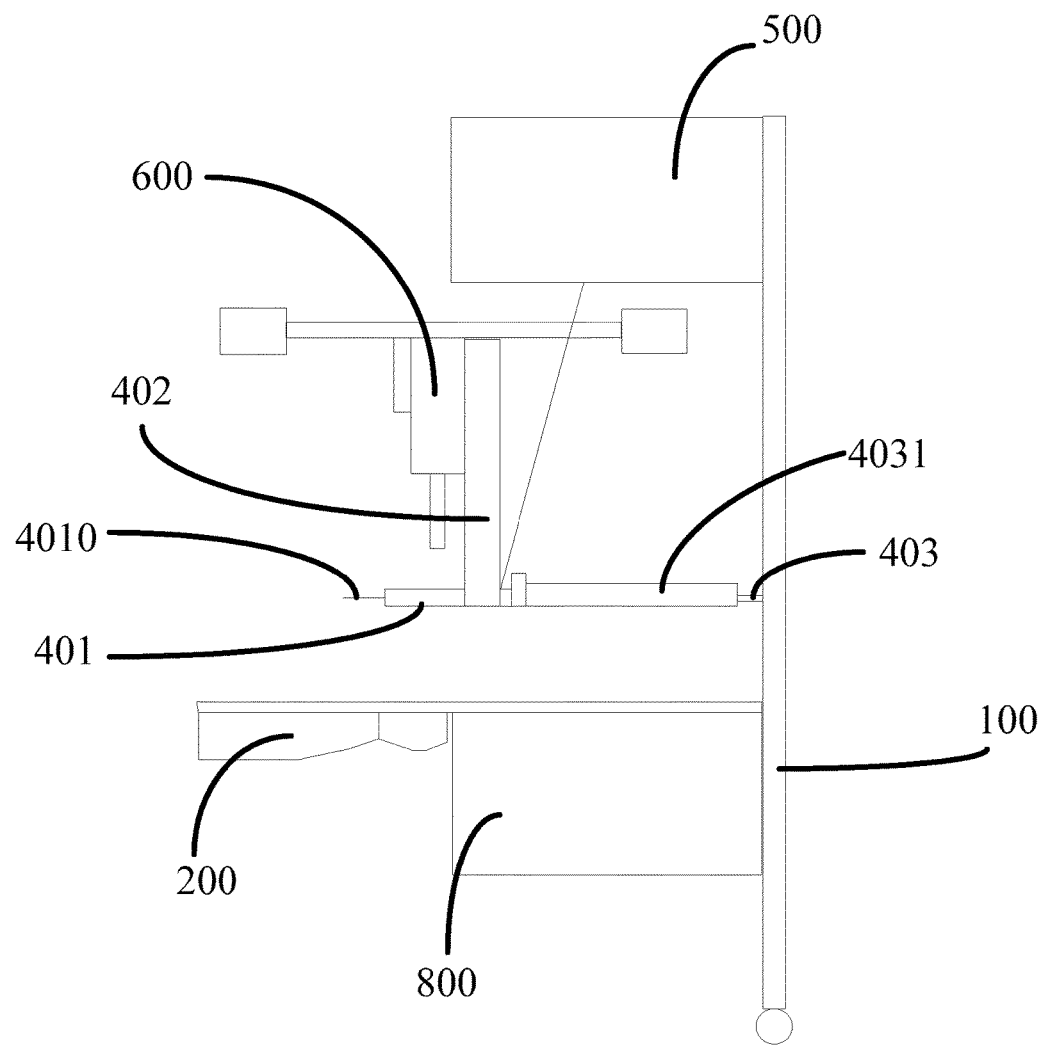
FIG. 2 is a schematic view showing the automatic needle insertion apparatus from another perspective according to one embodiment of the present disclosure.
Figure 3:
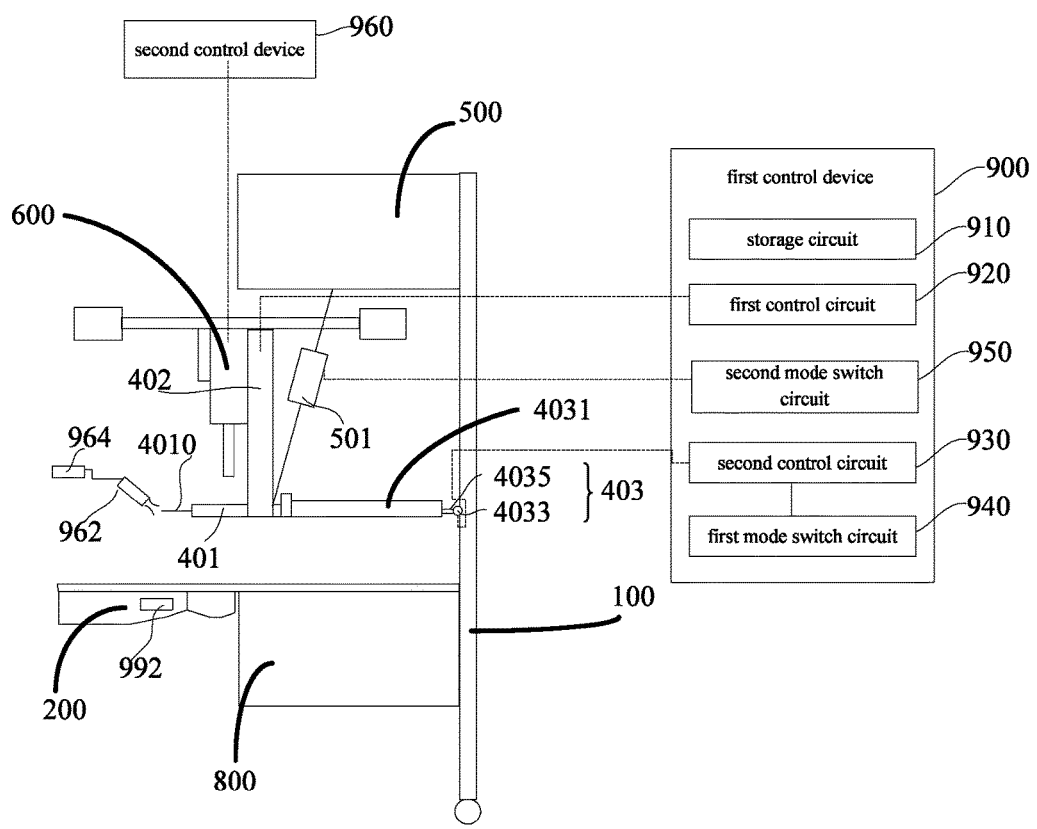
FIG. 3 is a schematic view showing the automatic needle insertion according to one embodiment of the present disclosure.

As shown in FIGS. 1 and 2, the present disclosure provides in some embodiments an automatic needle insertion apparatus, which includes: a frame 100; a bearing device 200 arranged on the frame 100 and configured to bear thereon a body part into which a needle is to be inserted; an acquisition device 300 arranged on the frame 100 and configured to acquire vascular information about the body part; a needle insertion device 400 arranged on the frame 100 and configured to execute a needle insertion operation and a needle withdrawal operation on the body part; and a first control device 900 (as shown in FIG. 3) connected to the needle insertion device 400 and the acquisition device 300 and configured to control an operating state of the needle insertion device 400 in accordance with the vascular information acquired by the acquisition device 300.

According to the automatic needle insertion apparatus in the embodiments of the present disclosure, the body part (e.g., arm) may be placed onto the bearing device 200, then the vascular information about the body part may be acquired by the acquisition device 300, and then the control mechanism may be used to adjust the position of the needle insertion device 400 and control the needle insertion device 400 to execute the needle insertion operation and the needle withdrawal operation in accordance with the vascular information about the body part. As a result, it is able to automatically insert the needle, reduce the human errors, and improve the working efficiency.

It should be appreciated that, the vascular information may include information about a vessel position and a vessel depth. The operating state of the needle insertion device 400 may include an adjustment position and an adjustment angle of the needle of the needle insertion device 400, as well as a series of actions of the needle insertion device 400 during an injection procedure, such as the needle insertion operation and the needle withdrawal operation.

In the automatic needle insertion apparatus, the acquisition device 300 may be a scanner. Alternatively, the acquisition device 300 may include an ultrasound image processing unit configured to send an ultrasound pulse to the body part, generate first image data in accordance with an ultrasound signal from the body part, and acquire the vascular information about the body part in accordance with the first image data; and/or an infrared scanning unit configured to generate second image data in accordance with an infrared ray radiated by the body part, and acquire the vascular information about the body part in accordance with the second image data.

In the embodiments of the present disclosure, one or two of a dedicated infrared thermal scanning unit and a color Doppler ultrasound image processing unit may be installed in the scanner. The ultrasound image processing unit may include an ultrasound transmitter configured to transmit an ultrasonic wave to the body part (a surface of the body part) for scanning, an ultrasound receiver configured to receive ultrasonic waves having different frequencies and reflected by the surface of the body part and a vessel, and a first image processor configured to generate the first image data in accordance with the received ultrasound signals from the body part. The infrared thermal scanning unit may include an infrared scanning module configured to receive an infrared ray irradiated by the body part (the surface of the body part), and a second image processor configured to generate the second image data in accordance with the received infrared ray. After the information collected by the infrared thermal scanning unit and the color Doppler ultrasound image processing unit have been processed, the acquisition device 300 may determine the vascular information such as the vessel position and the vessel depth.

It should be appreciated that, the conventional infrared thermal scanning unit and the color Doppler ultrasound image processing unit may be directly used in the embodiments of the present disclosure, so as to acquire the information about the vessel position and the vessel depth, thereby to reduce the errors during the needle insertion. During the actual application, apart from the infrared thermal scanning unit and/or the color Doppler ultrasound image processing unit, the acquisition device 300 may also be implemented in any other ways.

Alternatively, as shown in FIGS. 1 and 2, the needle insertion device 400 includes a syringe 401 and a mechanical arm 402. The mechanical arm 402 grips the syringe 501, and is configured to adjust a position of a needle 4010 of the syringe 401 and control the syringe 401 to execute the needle insertion operation and the needle withdrawal operation.

In the embodiments of the present disclosure, the syringe 401 may be gripped by the mechanical arm 402, so as to fine-adjust the position and angle of the needle 4010 of the syringe 401, thereby to enable the needle 4010 to be aligned to the vessel in the body part at an appropriate position.

It should be appreciated that, there may be various syringes 401 for different predetermined needle insertion modes, e.g., a syringe for bloodletting, a syringe for intravenous drip and a syringe for injection.

Alternatively, the first control device 900 includes a storage circuit 910 configured to store therein different predetermined needle insertion modes, and a first control circuit 920 connected to the mechanical arm 402, and configured to control the mechanical arm 402 to adjust the position of the needle 4010 of the syringe 401 and execute the needle insertion operation and the needle withdrawal operation in accordance with the vascular information about the body part and a current predetermined needle insertion mode.

In the embodiments of the present disclosure, a plurality of predetermined needle insertion modes may be stored in the first control device of the automatic needle insertion apparatus in advance, e.g., an infusion mode, a bloodletting mode and an injection mode, and these predetermined needle insertion modes correspond to different syringes 401 and different needle insertion and needle withdrawal operations. The predetermined needle insertion mode may be selected using a touch panel. After the desired needle insertion mode has been selected, the vascular information about the body part may be acquired by the acquisition device 300. Next, the mechanical arm 402 may be controlled in accordance with the vascular information and the current predetermined needle insertion mode, so as to adjust the position and angle of the needle 4010 of the syringe 401 corresponding to the current predetermined needle insertion mode. In this way, it is able to align the needle 4010 of the syringe 401 to the vessel, thereby to execute the needle insertion operation and the needle withdrawal operation corresponding to the current predetermined needle insertion mode.

Generally, in the bloodletting mode or injection mode, the syringe 401 includes a piston rod. Alternatively, as shown in FIG. 2, the needle insertion device 400 may further include a piston rod operation member 403 connected to a piston rod of the syringe 401 and configured to control a push-and-pull state of the piston rod of the syringe 401. The first control device further includes a second control circuit 930 connected to the piston rod operation member 403 and configured to control an operating state of the piston rod operation member 403 of the syringe 401 in accordance with the current predetermined needle insertion mode, so as to control the push-and-pull state of the piston rod of the syringe 401.

In the embodiments of the present disclosure, after the predetermined needle insertion modes such as the bloodletting mode and the injection mode have been selected using the touch screen, the operating state, e.g., a pushing operation or a pulling operation, of the piston rod operation member 403 of the syringe 401 may be controlled, so as to enable the needle insertion device 400 to execute the operations corresponding to the different predetermined needle insertion modes.

Generally, the syringe 401 in the infusion mode is not provided the piston rod. Alternatively, as shown in FIGS. 1 and 2, the automatic needle insertion apparatus may further include a plurality of liquid storage tanks 500 configured to store liquids therein, and a control valve 501 (as shown in FIG. 3) configured to control on and off states between each liquid storage tank 500 and the corresponding syringe 401. The liquids are delivered into different syringes 401 from different liquid storage tanks 500.

The first control device 900 may further include a first mode switch circuit 940 and a second mode switch circuit 950. The first mode switch circuit 940 is configured to send a control signal to the second control circuit in accordance with the current predetermined needle insertion mode, so as to control the mechanical arm 402 to adjust the position of the needle 4010 of the syringe 401 corresponding to the current predetermined needle insertion mode and execute the needle insertion operation and the needle withdrawal operation. The second mode switch circuit 950 is configured to control an operating state of the control valve, so as to enable the liquid storage tank 500 corresponding to the current predetermined needle insertion mode to be in communication with the syringe 401 corresponding to the current predetermined needle insertion mode.

In the embodiments of the present disclosure, several commonly-used liquids for infusion may be stored in the liquid storage tank 500. After the desired needle insertion mode (e.g., the infusion mode) has been selected using the touch screen, the opening state of the control valve is controlled by the second mode switch circuit, so as to enable the liquid storage tank 500 corresponding to the current predetermined needle insertion mode to be in communication with the syringe 401 corresponding to the current predetermined needle insertion mode. Next, the mechanical arm 402 is controlled by the first mode switch circuit in accordance with the selected predetermined needle insertion mode, so as to adjust the position of the needle 4010 of the syringe 401 corresponding to the current predetermined needle insertion mode, and then the mechanical arm 402 is controlled in accordance with the selected infusion mode to enable the syringe 401 to execute the needle insertion operation and the needle withdrawal operation. In this way, it is able to automatically insert the needle into the body of a patient after the predetermined needle insertion mode and the liquid have been selected.

Alternatively, the piston rod operation member 403 includes a driving motor 4033 and a transmission rod 4035 connected between the driving motor and the piston rod. The second control circuit is configured to control an operating state of the driving motor in accordance with the predetermined needle insertion mode, so as to control the push-and-pull state of the piston rod.

In the embodiments of the present disclosure, the operating state of the driving motor (e.g., a servo motor) may be controlled, so as to control the push-and-pull state of the piston rod, e.g., a pushing operation, a pulling operation, a pulling speed and a pulling speed of the piston rod. To be specific, the transmission rod may be a hydraulic rod, which may be driven by the driving motor so as to extend and retract. The hydraulic rod is connected to the piston rod of the syringe 401, so as to push and pull the piston rod of the syringe 401. It should be appreciated that, during the actual application, the piston rod operation member 401 may be in various forms, which will not be particularly defined herein.

Alternatively, as shown in FIG. 2, the piston rod operation member 403 may further include a stroke definition groove 4031, into which one end of the piston rod connected to the transmission rod is arranged, and which is configured to define a movement stroke of the piston rod, so as to prevent the piston rod from being offset during a push-and-pull procedure.

Alternatively, as shown in FIGS. 1 and 2, the automatic needle insertion apparatus further includes an adhesive bandage application device 600 and a second control device 960. The adhesive bandage application device 600 is configured to apply an adhesive bandage at a position of the body part into which the needle is inserted by the needle insertion device 400 before the needle withdrawal operation is executed by the needle insertion device 400. The second control device 960 is configured to, in accordance with the vascular information about the body part, adjust a position of the adhesive bandage application device 600 and control the adhesive bandage application device 600 to execute an adhesive bandage application operation.

In the embodiments of the present disclosure, before the needle withdrawal operation executed by the needle insertion device 400, the second control device may, in accordance with the vascular information about the body part, determine a position of the body part where the needle has been inserted, adjust the position of the adhesive bandage application device 600, and control the adhesive bandage application device 600 to execute the adhesive bandage application operation, so as to press the adhesive bandage onto the position of the body part where the needle has been inserted, thereby to improve the automatic needle insertion.

It should be appreciated that, in the embodiments of the present disclosure, the adhesive bandage application device 600 may be implemented by the mechanical arm which grips the adhesive bandage, and the structure of the adhesive bandage application device 600 is not particularly defined herein.

Alternatively, the automatic needle insertion apparatus may further include a sterilization device 962 configured to sterilize the body part where the needle is to be inserted by the needle insertion device 400 before the needle insertion operation, and a third control device 964 configured to, in accordance with the vascular information about the body part, adjust a position of the sterilization device and control the sterilization device to execute a sterilization operation.

It should be appreciated that, in the embodiments of the present disclosure, the sterilization device may be implemented by the mechanical arm 402 which grips aseptic cotton, or by spraying a disinfectant onto the body part where the needle is to be inserted. The structure of the sterilization device is not particularly defined herein.

In addition, the automatic needle insertion apparatus may further include an adjustment device connected to the bearing device 200 and configured to adjust a position of the bearing device 200, so as to move the body part to a predetermined position. In this way, it is able to adjust the position of the bearing device 200 through the adjustment device, so as to place the body part to be at an appropriate position, thereby to facilitate the acquisition of the vascular information as well as the needle insertion operation and the needle withdrawal operation.

It should be appreciated that, the bearing device 200 may include an inflatable air bag into which the body part (e.g., arm) may be placed. In the case that the air bag is inflated to a predetermined pressure, it may function as a tourniquet, so as to fill the vessel in the body part with blood, thereby to facilitate the bloodletting procedure. Alternatively, the inflatable air bag is provided with a pressure sensor 992, so as to accurately control the pressure in the inflatable air bag. Of course, during the actual application, the bearing structure 200 may be of any other structures, which are not particularly defined herein.

It should be further appreciated that, as shown in FIG. 1, the automatic needle insertion apparatus may further include a blood storage tank 800 configured to store therein the blood drawn from the body part. After the bloodletting operation through the syringe 401, the syringe filled with the blood may be placed into the blood storage tank 800.

In addition, as shown in FIGS. 1 and 2, the adjustment device includes supporters 701 connected to two sides of the bearing device 200 respectively, sliding rails 702 arranged on the frame 100 and located at two sides of the bearing device 200, and stoppers 705 (as shown in FIG. 1) arranged on the frame 100 and configured to limit positions of the supporters 701 on the sliding rails 702 in the case that the bearing device 200 moves to a predetermined position. The supporters 701 are movably arranged onto the sliding rails 702 respectively.

In the embodiments of the present disclosure, the supporters may be moved up and down along the sliding rails on the frame 100, so as to adjust the bearing device 200 to an appropriate position. After the bearing device 200 is located at the appropriate position, the supporters may be limited by the stoppers. The supporters, the sliding rails and the stoppers may be implemented in various forms, and their structures are not particularly defined herein, as long as the position of the bearing device 200 may be adjusted.

Alternatively, a display screen may also be arranged on the frame 100. In this way, the patient may browse a webpage or watch a video during the needle insertion, so as to relieve the mental pressure.

The operating procedure of the automatic needle insertion apparatus will be described hereinafter.

At first, the needle 4010 of the syringe 401 may be mounted by a medical staff, and the predetermined needle insertion mode may be selected. The patient may place his arm onto the bearing device 200, adjust the position of the arm by adjusting the supporters, and limit the supporters through the stoppers.

Next, the vessel position and the vessel depth may be determined by the dedicated infrared thermal scanning unit and/or color Doppler ultrasound image processing unit installed in the acquisition device 300.

Next, the needle 4010 of the syringe 401 in the current predetermined needle insertion mode may be fine-adjusted through the mechanical arm 402, so as to be aligned to the vessel. After the liquid has been selected, the needle may be inserted into the body part of the patient so as to give the patient an intravenous drip.

After the intravenous drip has been completed, the adhesive bandage may be applied onto the wound by the adhesive bandage application device 600, and the needle 4010 of the syringe 401 may be withdrawn through the mechanical arm 402. After the patient moves his arm away from the bearing device 200, the needle 4010 may be removed by the medical staff from the syringe.

The above are merely the preferred embodiments of the present disclosure. It should be appreciated that, a person skilled in the art may make further modifications and improvements without departing from the principle of the present disclosure, and these modifications and improvements shall also fall within the scope of the present disclosure.

What is claimed is:

1. An automatic needle insertion apparatus, comprising:
a frame;
a bearing device on the frame and configured to bear thereon a body part into which a needle is to be inserted;
an acquisition device on the frame and configured to acquire vascular information of the body part;
a needle insertion device on the frame and configured to execute a needle insertion operation and a needle withdrawal operation on the body part; and
a first control device connected to the needle insertion device and the acquisition device and configured to control an operating state of the needle insertion device in accordance with the vascular information acquired by the acquisition device, the automatic needle insertion apparatus further comprises an adjustment device connected to the bearing device and configured to adjust a position of the bearing device, so as to move the body part to a predetermined position, wherein the adjustment device comprises:

supporters connected to two sides of the bearing device respectively;

sliding rails on the frame and at two sides of the bearing device, the supporters being movably arranged onto the sliding rails respectively; and stoppers on the frame and configured to limit positions of the supporters on the sliding rails in the case that the bearing device moves to a predetermined position.

2. The automatic needle insertion apparatus according to claim 1, wherein the acquisition device comprises:

an ultrasound image processing unit configured to send an ultrasound pulse to the body part, generate first image data in accordance with an ultrasound signal from the body part, and acquire the vascular information of the body part in accordance with the first image data; and/or an infrared scanning unit configured to generate second image data in accordance with an infrared ray radiated by the body part, and acquire the vascular information of the body part in accordance with the second image data.

3. The automatic needle insertion apparatus according to claim 1, wherein the needle insertion device comprises:

a syringe; and a mechanical arm configured to grip the syringe and adjust a position of a needle of the syringe and control the syringe to execute the needle insertion operation and the needle withdrawal operation; and the first control device comprises:

a storage circuit configured to store therein different predetermined needle insertion modes; and a first control circuit connected to the mechanical arm, and configured to control the mechanical arm to adjust the position of the needle of the syringe and execute the needle insertion operation and the needle withdrawal operation in accordance with the vascular information of the body part and a current predetermined needle insertion mode.

4. The automatic needle insertion apparatus according to claim 3, wherein the needle insertion device further comprises:

a piston rod operation member connected to a piston rod of the syringe and configured to control a push-and-pull state of the piston rod of the syringe, and the first control device further comprises:

a second control circuit connected to the piston rod operation member and configured to control an operating state of the piston rod operation member of the syringe in accordance with the current predetermined needle insertion mode, so as to control the push-and-pull state of the piston rod of the syringe.

5. The automatic needle insertion apparatus according to claim 4, wherein the piston rod operation member comprises:

a driving motor; and a transmission rod connected between the driving motor and the piston rod, wherein the second control circuit is configured to control an operating state of the driving motor in accordance with the predetermined needle insertion mode, so a to control the push-and-pull state of the piston rod.

6. The automatic needle insertion apparatus according to claim 5, wherein the piston rod operation member further comprises:

a stroke definition groove, into which one end of the piston rod connected to the transmission rod is arranged, and which is configured to define a movement stroke of the piston rod, so as to prevent the piston rod from being offset during a push-and-pull procedure.

7. The automatic needle insertion apparatus according to claim 3, further comprising:

a plurality of liquid storage tanks configured to store liquids therein, the liquids being delivered into different syringes from different liquid storage tanks; and a control valve configured to control on and off states between each liquid storage tank and the corresponding syringe, and the first control device further comprises:

a first mode switch circuit configured to send a control signal to the second control circuit in accordance with the current predetermined needle insertion mode, so as to control the mechanical arm to adjust the position of the needle of the syringe corresponding to the current predetermined needle insertion mode and execute the needle insertion operation and the needle withdrawal operation; and a second mode switch circuit configured to control an operating state of the control valve, so as to enable the liquid storage tank corresponding to the current predetermined needle insertion mode to be in communication with the syringe corresponding to the current predetermined needle insertion mode.

8. The automatic needle insertion apparatus according to claim 1, further comprising a blood storage tank configured to store therein blood drawn from the body part.

9. The automatic needle insertion apparatus according to claim 1, wherein the bearing device is an inflatable air bag with a pressure sensor.

* * * * *